United States Patent
Lopath

(10) Patent No.: US 10,010,449 B2
(45) Date of Patent: Jul. 3, 2018

(54) CORNEAL CROSSLINKING WITH OXYGENATION

(71) Applicant: TECLens, LLC, St. James, NY (US)

(72) Inventor: Patrick David Lopath, Stamford, CT (US)

(73) Assignee: TECLens, LLC, St. James, NY (US)

( * ) Notice: Subject to any disclaimer, the term of this patent is extended or adjusted under 35 U.S.C. 154(b) by 40 days.

(21) Appl. No.: 14/976,013

(22) Filed: Dec. 21, 2015

(65) Prior Publication Data

US 2016/0175147 A1   Jun. 23, 2016

Related U.S. Application Data

(60) Provisional application No. 62/095,288, filed on Dec. 22, 2014.

(51) Int. Cl.

| | |
|---|---|
| *A61F 9/01* | (2006.01) |
| *A61F 9/00* | (2006.01) |
| *A61N 5/06* | (2006.01) |
| *A61F 9/007* | (2006.01) |
| *A61K 9/00* | (2006.01) |
| *A61F 9/009* | (2006.01) |
| *A61F 9/008* | (2006.01) |

(52) U.S. Cl.
CPC .......... *A61F 9/0017* (2013.01); *A61F 9/0079* (2013.01); *A61N 5/062* (2013.01); *A61F 9/009* (2013.01); *A61F 2009/00872* (2013.01); *A61K 9/0048* (2013.01)

(58) Field of Classification Search
CPC ........ A61F 9/0079; A61F 9/008; A61F 9/009; A61F 9/0017; A61F 9/013; A61F 2009/00872; A61N 5/062; A61N 2005/0648; G02C 7/04
USPC .............. 604/300; 606/4, 5, 41; 607/88
See application file for complete search history.

(56) References Cited

U.S. PATENT DOCUMENTS

| | | | |
|---|---|---|---|
| 6,221,028 B1 * | 4/2001 | Lieberman | A61B 3/0008 351/200 |
| 6,592,574 B1 * | 7/2003 | Shimmick | A61B 3/107 351/206 |
| 8,366,689 B2 * | 2/2013 | Marshall | A61F 9/008 604/290 |

(Continued)

FOREIGN PATENT DOCUMENTS

| | | |
|---|---|---|
| DE | 102010016629 A1 | 10/2011 |
| EP | 112658 A2 | 7/1984 |

(Continued)

OTHER PUBLICATIONS

Muller et al.., Maximizing Efficacy of Accelerated Transepithelial Cross-linking, avedro, Waltham, MA (2013).

(Continued)

*Primary Examiner* — Nathan R Price
*Assistant Examiner* — Gerald Landry, II
(74) *Attorney, Agent, or Firm* — Lerner, David, Littenberg, Krumholz & Mentlik, LLP

(57) ABSTRACT

In corneal crosslinking by applying a photoactivated crosslinking facilitator such as riboflavin to the cornea and irradiating the cornea with light, the cornea is contacted with a liquid (33) containing a source of oxygen during irradiation. The liquid transfers oxygen to the cornea to facilitate crosslinking.

17 Claims, 1 Drawing Sheet

(56) References Cited

U.S. PATENT DOCUMENTS

| | | | | |
|---|---|---|---|---|
| 8,562,660 B2* | 10/2013 | Peyman | | A61N 5/062 607/88 |
| 8,574,277 B2* | 11/2013 | Muller | | A61F 9/0008 606/4 |
| 8,870,934 B2* | 10/2014 | Muller | | A61F 9/0008 607/88 |
| 2006/0135957 A1* | 6/2006 | Panescu | | A61B 18/14 606/41 |
| 2007/0038271 A1* | 2/2007 | Cole | | A61N 5/062 607/88 |
| 2007/0142828 A1* | 6/2007 | Peyman | | A61F 7/007 606/12 |
| 2008/0208177 A1* | 8/2008 | Mrochen | | A61F 9/008 606/5 |
| 2010/0274228 A1* | 10/2010 | Mrochen | | A61F 9/009 604/541 |
| 2011/0264082 A1* | 10/2011 | Mrochen | | A61F 9/008 606/5 |
| 2012/0303008 A1* | 11/2012 | Muller | | A61F 9/013 606/5 |
| 2013/0103009 A1* | 4/2013 | Gooding | | A61F 9/00827 606/4 |
| 2013/0211389 A1* | 8/2013 | Chuck | | A61F 9/0079 606/5 |
| 2013/0338650 A1* | 12/2013 | Jester | | A61F 9/00804 606/5 |
| 2014/0010848 A1* | 1/2014 | Kheir | | A61K 9/0019 424/400 |
| 2014/0148687 A1* | 5/2014 | Keenan | | A61K 49/223 600/420 |
| 2014/0379054 A1* | 12/2014 | Cooper | | A61F 9/0079 607/90 |
| 2015/0005754 A1* | 1/2015 | Gooding | | A61F 9/00827 606/6 |
| 2015/0126921 A1* | 5/2015 | Rubinfeld | | A61K 9/0048 604/20 |

FOREIGN PATENT DOCUMENTS

| | | |
|---|---|---|
| EP | 1970034 A1 | 9/2008 |
| WO | 2012095876 A1 | 7/2012 |
| WO | 2013148896 A1 | 10/2013 |
| WO | 2014210152 A2 | 12/2014 |

OTHER PUBLICATIONS

International Search Report for Application No. PCT/US2015/067107 dated Mar. 16, 2016.
Extended European Search Report for Application No. EP17184979 dated Dec. 15, 2017.

* cited by examiner

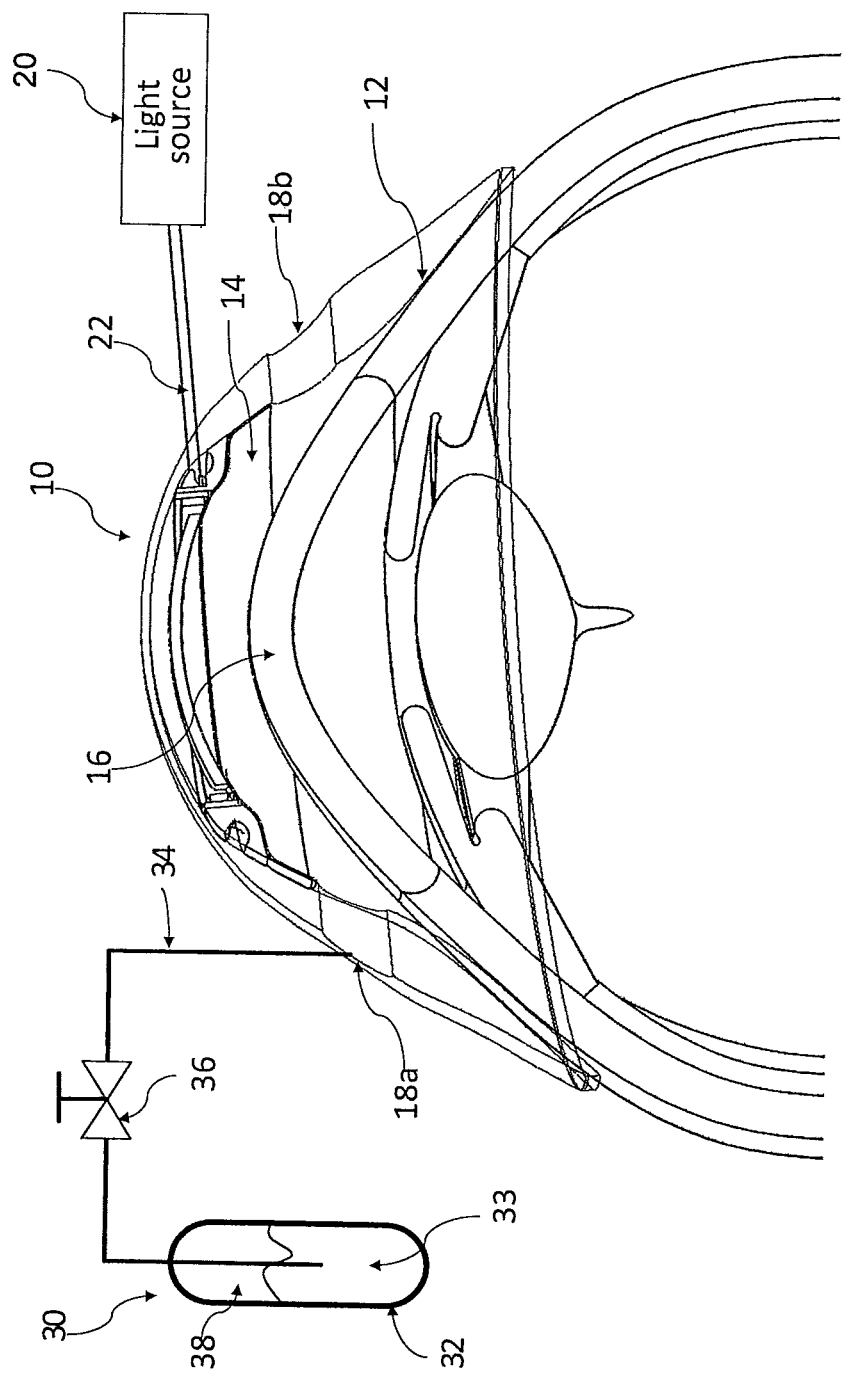

CORNEAL CROSSLINKING WITH OXYGENATION

CROSS-REFERENCE TO RELATED APPLICATIONS

The present application claims the benefit of the filing date of U.S. Patent Application No. 62/095,288, filed Dec. 22, 2014, the disclosure of which is hereby incorporated by reference herein.

BACKGROUND OF THE INVENTION

The present invention relates to methods, apparatus, and compositions for treating conditions of the cornea.

The cornea in the eye of a human or other mammalian subject can be modified by crosslinking the collagen within the cornea. A photoactivated crosslinking facilitator such as riboflavin is applied to the cornea. Light at a wavelength selected to activate the crosslinking facilitator is applied. Where the crosslinking facilitator is riboflavin, the light typically is ultraviolet ("UV") or blue light. The activated facilitator causes crosslinking of the collagen within the cornea. The crosslinking changes the mechanical properties of the cornea. These changes can result in stabilization of pathological conditions, such as keratoconus, or in alterations to the shape of the cornea. This technique can be used to correct defects in vision such as myopia, hyperopia, or astigmatism. In some applications, the light is applied as a beam directed into the eye from a device remote from the eye.

In other applications, the light is directed into the cornea from a device that sits on the eye. For example, as disclosed in U.S. patent application Ser. No. 14/314,518 ("the '518 Application") and U.S. Provisional Patent Application No. 61/839,016 ("the '016 Provisional"), the disclosures of which are hereby incorporated by reference herein and copies of which are annexed hereto as a part of this disclosure, light can be applied to the eye through a structure having a form, size, and shape resembling that of a contact lens such as a scleral contact lens. The structure may incorporate an optically dispersive element. Light may be directed into the dispersive element and dispersed so that the dispersed light passes into the eye from the dispersive element. This arrangement has numerous advantages. For example, the patient may be able to close his or her eye during the treatment, so that the structure is disposed between the eyelid and the eye. This helps to maintain adequate moisture on the surface of the cornea.

As also disclosed in the foregoing '518 Application and '016 Provisional, such a structure may be provided with one or more ports communicating with the surface of the device that overlies the cornea. Optionally, a liquid can be supplied through the ports so that the space between the device and the cornea remains filled with the liquid.

The degree of crosslinking depends in part upon the amount of crosslinking facilitator present in the collagen during light application and in part upon the amount of illumination applied to the eye. However, these factors alone apparently do not control the degree of crosslinking achieved.

Although the present invention is not limited by any theory of operation, current theory holds the oxygen present in the collagen layers of the cornea plays a role in the crosslinking reaction and that the crosslinking reaction can be limited by the amount of oxygen present. In the present disclosure, the concentration of oxygen in the cornea is referred to as the oxygen saturation of the cornea. Muller et al., Maximizing Efficacy of Accelerated Transepithelial Cross-linking, reports that when riboflavin is present in the cornea, the oxygen saturation of the cornea decreases rapidly upon irradiation of the cornea with UV light, and reports that crosslinking can be enhanced by exposing the cornea to gaseous oxygen rather than air during irradiation. However, further improvement would be desirable.

SUMMARY OF THE INVENTION

One aspect of the invention provides a composition comprising a liquid pharmacologically acceptable for contact with the cornea of an eye of a mammalian subject, and a source of oxygen included in the liquid, for use in treatment of a conditions of the cornea. In certain embodiments, the source of oxygen may be a perfluorocarbon.

A further aspect of the invention provides apparatus for corneal crosslinking. Apparatus according to this aspect of the invention desirably includes a structure having an interior surface adapted to overlie a surface of the cornea of an eye of a mammalian subject. The apparatus desirably further includes a liquid supply constructed and arranged to supply a liquid including a source of oxygen to a space between the cornea and the structure while the structure is overlying the cornea.

A still further aspect of the invention provides methods of treating conditions of the cornea such as keratoconus, hyperopia, myopia, and astigmatism by crosslinking collagen in the cornea. A method according to this aspect of the invention desirably includes the steps contacting a cornea of an eye of the subject with a photoactivated crosslinking facilitator, and irradiating the cornea with light at a wavelength that activates the crosslinking facilitator. Most preferably, the method according to this aspect of the invention includes the further step of contacting the cornea with a liquid including a source of oxygen during the irradiation step. The composition and apparatus according to the foregoing aspects of the invention may be used in this method.

BRIEF DESCRIPTION OF THE DRAWINGS

FIG. 1 is a diagrammatic, partially sectional view depicting apparatus according to one embodiment of the invention.

DETAILED DESCRIPTION

One aspect of the present invention provides methods of crosslinking collagen in the cornea of an eye of a mammalian subject. A method according to this aspect of the invention desirably includes the steps of contacting a cornea of an eye of the subject with a photoactivated crosslinking facilitator, and irradiating the cornea with light at a wavelength that activates the crosslinking facilitator. The method according to this aspect of the invention most preferably also includes the step of contacting the cornea with a liquid including a source of oxygen during the irradiating step. Where a structure overlies the eye during the irradiating step, the liquid may be disposed in a space between the structure and the cornea. For example, where the light is applied by a irradiation device including a structure adapted to overlie the eye and direct light into the eye, such as a device according to the '518 Application, the liquid may be disposed in the space between this device and the cornea. The liquid releases oxygen to the cornea and helps to maintain the oxygen saturation of the cornea during the irradiating step. The liquid may be renewed during the irradiating step as, for example, by supplying fresh liquid to the space through one or more ports in the structure. The liquid as referred to herein is a liquid other than the tears that are secreted by the subject. Stated another way, the liquid as referred to herein typically is an exogenous liquid. Natural tears in contact with atmospheric air under normal atmospheric conditions contain some dissolved oxygen that serves as a natural oxygen source. Thus, natural tears of a subject under normal atmospheric conditions have some ability to transfer oxygen to the cornea. Most desirably, the liquid contacted with the cornea embodiments according to the present invention has an ability to transfer oxygen to the cornea that is greater than that of natural tears under normal atmospheric conditions. The exogenous liquid may mix with natural tears during contact with the cornea.

A further aspect of the invention provides additional methods of crosslinking collagen in the cornea of an eye of a mammalian subject. A method according to this aspect of the invention desirably includes the steps of contacting the cornea with a liquid including a source of oxygen and a photoactivated crosslinking facilitator and then irradiating the cornea with light at a wavelength that activates the crosslinking facilitator. The liquid transfers both oxygen and the crosslinking facilitator to the cornea. For example, the liquid may be maintained in contact with the cornea using a structure having a surface adapted to overlie the cornea so that there is a space between the structure and the cornea. The structure used in this step may be an irradiation device which is subsequently used to irradiate the cornea, or may be a separate structure that is removed before irradiating the cornea. The liquid may be maintained in the space for a time sufficient to reach the desired crosslinking facilitator saturation. This time will depend in part upon the condition of the cornea. Where the epithelial layer of the cornea is intact, this time typically is on the order of an hour to 90 minutes. Where the epithelial layer of the cornea has been removed, this time typically is on the order of an hour or less as, for example, 30 minutes or less. Here again, the liquid may be renewed during this time by supplying fresh liquid to the space. The fresh liquid may be supplied through a port in the structure communicating with the space.

The foregoing aspects of the present invention optionally may be combined with one another, so that the cornea is exposed to a first liquid containing both the crosslinking facilitator and an oxygen source before irradiation, and to a second liquid containing an oxygen source during the irradiation. Typically, the liquid applied during the irradiation does not contain the crosslinking facilitator. The facilitator typically absorbs UV light. Therefore, facilitator overlying the cornea in the liquid present during irradiation will reduce the intensity of the light reaching the cornea. However, this effect can be mitigated by minimizing the thickness of the liquid layer. Also, the intensity of the applied light can be increased to compensate for light absorption by facilitator in the liquid layer. Where light absorption by the liquid layer can be tolerated, the facilitator can be included in the liquid applied during irradiation. Facilitator in this liquid can be absorbed by the cornea during irradiation and may enhance the crosslinking.

Preferred embodiments of the foregoing methods desirably provide oxygenation saturation of the cornea greater than that which would be present without application of the oxygen-containing liquid. For example, the oxygen saturation may be brought to at a level at or above a normal oxygen saturation level of the cornea prior to irradiation. As used in this disclosure, the term "normal oxygen saturation level" refers to the level of oxygen saturation that is present during normal conditions, with the subject exposed to room air. The oxygen saturation of the cornea typically decreases during irradiation. However, the oxygen saturation of the cornea is still maintained at a higher level than would occur without use of the oxygen-containing liquid. The ability to maintain oxygen saturation of the cornea is particularly useful where irradiation is applied using a device which overlies the eye. Such a device may restrict oxygen transfer from the atmosphere to the cornea. Use of the oxygen-containing liquid counteracts this effect. This advantage is particularly significant where the irradiation is performed over a period of several minutes or more as, for example, about 30 minutes. In other embodiments, the enhanced oxygen saturation level can permit faster crosslinking through the use of higher light intensity and thus provide shorter irradiation time. In some embodiments, the irradiation can be applied in pulses. The oxygen saturation may decrease during each pulse and increase during intervals between pulses. The use of the oxygen-containing liquid can allow efficient crosslinking with an increased duty cycle, higher intensity during pulses, or both.

A further aspect of the invention provides compositions for use in treatments such as those discussed above. The composition according to this aspect of the invention desirably comprises a liquid pharmacologically acceptable for contact with the cornea of an eye of a mammalian subject, the liquid including a source of oxygen. The composition may also contain a photoactivated crosslinking facilitator dispersed in the liquid. As used in this disclosure, the term "source of oxygen" refers to a substance or moiety that, under conditions prevailing in the vicinity of the cornea, will supply oxygen to the cornea. In one embodiment, the liquid may contain dissolved oxygen as the source of oxygen. The liquid desirably is pharmaceutically acceptable for contact with the surface of the cornea. Where the liquid is to be applied during irradiation, the liquid desirably is transparent to UV light. As used in this disclosure, the term "transparent" does not require perfect transparency or zero light absorption. One class of liquids that is particularly suitable for carrying dissolved oxygen consists of perfluorocarbons. Examples of pharmaceutically acceptable perfluorocarbons include materials of the type that can be used as oxygen carriers in blood substitutes. Also, perfluorocarbons of the type used as respiratory aids or lung lavage agents can be employed. Still further, the liquid may include perfluorocarbons of the type used in ophthalmology, such as those used for treatment of retinal detachment and for foreign body removal. The liquid may include the perfluorocarbon with dissolved oxygen and also may include other pharmaceutically acceptable materials. For example, the perfluorocarbon may be provided as an emulsion with an aqueous or other liquid phase. In other embodiments, the perfluorocarbon with oxygen dissolved therein may constitute the entire liquid.

In other embodiments, the liquid may be an aqueous solution containing dissolved oxygen, with or without the crosslinking facilitator. The liquid may be supersaturated with oxygen under the conditions prevailing during contact with the cornea. Typically, the liquid will be at or near body temperature and atmospheric pressure during contact with the cornea.

Yet another aspect of the invention provides apparatus for treating a mammalian subject as, for example, in the methods as discussed above. Apparatus according to this aspect of the invention desirably includes a structure having an interior surface adapted to overlie a surface of the cornea of an eye of the subject. The apparatus desirably also includes a liquid supply constructed and arranged to supply a liquid having a source of oxygen dispersed therein to a space between the cornea and the structure while the structure is overlying the cornea. In one example, a structure 10 (FIG. 1) has a shape and size similar to that of a conventional scleral contact lens. The structure includes an interior surface 12 with a shape adapted to contact the sclera of the eye and to leave a space 14 between the cornea 16 and the interior surface. The structure has one or more ports 18 communicating with the interior surface. In the particular embodiment depicted in FIG. 1, the ports include an inlet port 18a and an outlet port 18b. In this embodiment, the structure includes optical elements adapted to direct light such as ultraviolet light from a light source 20 such as a laser into the cornea while the structure is in place on the cornea. The optical elements may be as described in the aforementioned publications. For example, the optical elements may include one or more optical fibers 22 in optical communication with the light source, and may also include reflective elements (not shown) for routing the light from the fibers into the cornea. The optical elements may include optically scattering elements such as diffuse reflecting surfaces, scattering transmissive elements and the like, as well as a wall defining an aperture (not shown) for limiting light application to a desired region of the cornea. In other embodiments, the elements for directing the light into the cornea may include light-emitting elements such as light-emitting diodes.

In the embodiment of FIG. 1, a liquid supply 30 includes a reservoir 32 containing the liquid 33. Reservoir 32 is connected to the inlet port 18a of the structure by one or more conduits 34 so that liquid can flow from the reservoir to the space 14 between the structure and the cornea. The liquid may flow through the space 14 and exit through outlet port 18b. Optionally, the liquid supply may include elements such as pumps (not shown) and one or more valves 36 for controlling the liquid flow.

In the embodiment depicted, the liquid supply is arranged to supply the liquid in a condition such that the liquid will be supersaturated with oxygen when it enters space 14. In this embodiment, reservoir 32 is arranged to hold the liquid 33 at a superatmospheric pressure. Thus, if the liquid is placed within the reservoir in a condition where it has a dissolved oxygen level above its saturation level at atmospheric pressure and body temperature, the liquid will remain at this dissolved oxygen level until it exits the reservoir and passes into space 14. The headspace 38 above the liquid level in the reservoir may be filled with an oxygen-containing gas such as pure oxygen, compressed air, or another oxygen-containing gas mixture. In other embodiments, the reservoir may be equipped with a device for continually contacting the liquid in the reservoir with an oxygen containing gas as, for example, a bubbler for passing the oxygen-containing gas through the mixture. Still other embodiments can include a chiller for maintaining the liquid at a low temperature. In still other embodiments, the liquid may be stored in a condition where it is not supersaturated and brought to an elevated oxygen level enroute from the reservoir to the space 14. For example, the liquid supply 30 may include pump (not shown) for pressurizing the liquid as it passes out of the reservoir 32, and a gas/liquid contacting device such as a bubbler for introducing oxygen into the liquid while it is under superatmospheric pressure.

The number of ports can be varied. For example, only an input port may be provided. Liquid introduced into the space may pass out of the space at the periphery of the structure.

In still other embodiments, the liquid supply may include a simple liquid dispensing device such as an eyedropper or pipette containing the aforementioned liquid. The eyedropper or pipette can be used to dispense the liquid into the port manually.

Optionally, the structure of the irradiation device also may be used to confine a liquid containing the crosslinking facilitator and a source of oxygen prior to the irradiation step. In other embodiments, a similar structure without the optical elements may be used for this function. In a further variant, the irradiating step can be performed using light directed into the eye from a source remote from the eye. For example, the oxygen-containing liquid may be applied directly to the eye, without a confining structure. In other variants, a structure which is translucent or transparent to the light may overlie the eye and confine the liquid, and the remote source may direct light through the structure and the liquid.

The compositions and apparatus discussed above also may be applied to treatment of other conditions of the cornea such as infectious keratitis where corneal crosslinking is not required. Therefore, the liquid applied to the eye during irradiation desirably does not include a photoactivated crosslinking facilitator such as riboflavin. Also, in treatment of conditions where corneal crosslinking is not required, the eye is not contacted with a photoactivated crosslinking facilitator prior to irradiation.

The invention claimed is:

1. A method of crosslinking collagen in the cornea of an eye of a mammalian subject comprising the steps of:
    (a) contacting a cornea of an eye of the subject with a photoactivated crosslinking facilitator, and irradiating the cornea with light at a wavelength that activates the crosslinking facilitator; and
    (b) during the irradiating step, maintaining a liquid including a perfluorocarbon having oxygen dissolved therein in a space between a structure overlying the cornea and the cornea so that the liquid contacts the cornea and the liquid transfers oxygen to the cornea during the irradiating step.

2. A method as claimed in claim 1 wherein the structure is in the form of a shell less than about 3 mm thick and having a shape conforming to the shape of an anterior surface of the eye.

3. A method as claimed in claim 2 wherein the irradiating step includes directing light into the cornea using the structure overlying the cornea.

4. Apparatus for corneal crosslinking comprising:
    (a) a structure having an interior surface adapted to overlie a surface of the cornea of an eye of a mammalian subject;
    (b) a source of light; and
    (c) a liquid supply constructed and arranged to supply a liquid including a perfluorocarbon having oxygen dissolved therein to a space between the cornea and the structure while the structure is overlying the cornea and while light is passing from the light source to the cornea.

5. Apparatus as claimed in claim 4 wherein the structure is adapted to direct light from the light source into the cornea.

6. Apparatus as claimed in claim 4 or claim 5 wherein the structure has a form corresponding to the form of a contact lens.

7. A method as claimed in claim 1 wherein the structure has a form corresponding to the form of a contact lens.

8. A method as claimed in claim 2 or claim 7 wherein the step of maintaining a liquid includes introducing the liquid into the space and passing the liquid out of the space during the irradiating step.

9. A method as claimed in claim 8 wherein the step of introducing the liquid into the space includes introducing the liquid through an inlet port in the structure.

10. A method as claimed in claim 9 wherein the step of passing liquid out of the space includes passing the liquid out of the space at a periphery of the structure.

11. A method as claimed in claim 9 wherein the step of passing liquid out of the space includes passing the liquid out of the space through an outlet port in the structure.

12. A method as claimed in claim 1 wherein the structure allows the subject to close the eye during the irradiation step so that when the eye is closed the structure is disposed between the eyelid and the eye.

13. Apparatus as claimed in claim 4 further comprising one or more optical fibers extending from the light source to the structure and wherein the structure includes one or more an optical scattering element in optical communication with the fiber, the structure being arranged to align the scattering element with the cornea so that light directed from the source to the one or more optical fibers will pass into scattering element and light scattered by the scattering element will pass into the cornea.

14. Apparatus as claimed in claim 13 wherein the structure includes an inlet port communicating with the space and the liquid source includes one or more conduits connected to the inlet port.

15. Apparatus as claimed in claim 14 wherein the structure is in the form of a shell less than about 3 mm thick and having a shape conforming to the shape of an anterior surface of the eye.

16. Apparatus as claimed in claim 14 wherein the structure includes an outlet port communicating with the space.

17. Apparatus as claimed in claim 4 wherein the structure is translucent or transparent and the light source is disposed remote from the structure and arranged to direct light through the structure and the liquid.

* * * * *